United States Patent [19]

Harris

[11] 4,188,927
[45] Feb. 19, 1980

[54] MULTIPLE SOURCE ELECTROSURGICAL GENERATOR

[75] Inventor: Frank W. Harris, Boulder, Colo.

[73] Assignee: Valleylab, Inc., Boulder, Colo.

[21] Appl. No.: 869,008

[22] Filed: Jan. 12, 1978

[51] Int. Cl.² .................. A61B 17/36; A61N 3/02
[52] U.S. Cl. ...................... 128/303.14; 128/303.17
[58] Field of Search .............. 128/303.13, 303.14, 128/303.17, 303.18, 421, 422, 423

[56] References Cited

U.S. PATENT DOCUMENTS

| | | | |
|---|---|---|---|
| 1,813,902 | 7/1931 | Bovie | 128/421 |
| 1,945,867 | 2/1934 | Rawls | 128/303.14 |
| 3,058,470 | 10/1962 | Seeliger et al. | 128/303.14 |
| 3,163,165 | 12/1964 | Isikaws | 128/303.17 |
| 3,515,943 | 6/1970 | Warrington | 317/27 |
| 3,601,126 | 8/1971 | Estes | 128/303.14 |
| 3,699,967 | 10/1972 | Anderson | 128/303.14 |
| 3,812,858 | 5/1974 | Oringer | 128/303.14 |
| 3,848,600 | 11/1974 | Patrick, Jr. et al. | 128/303.13 |
| 3,923,063 | 12/1975 | Andrews et al. | 128/303.14 |
| 3,963,030 | 6/1976 | Newton | 128/303.17 |
| 4,114,623 | 9/1978 | Meinke et al. | 128/303.14 |

FOREIGN PATENT DOCUMENTS

| | | | |
|---|---|---|---|
| 13888 | 10/1971 | Australia | 128/417 |
| 1149832 | 6/1963 | Fed. Rep. of Germany | 128/303.13 |
| 2504280 | 8/1976 | Fed. Rep. of Germany | 128/303.14 |
| 1275415 | 10/1961 | France | 128/303.14 |
| 855459 | 11/1960 | United Kingdom | 128/303.14 |

*Primary Examiner*—Lee S. Cohen
*Attorney, Agent, or Firm*—Gerald J. Ferguson, Jr.; Joseph J. Baker

[57] ABSTRACT

A multiple source electrosurgical generator wherein one of the sources may be optimized for desiccation of the patient's tissue, another source may be optimized for fulguration thereof and a third source may be optimized for cutting. All sources operate into a common output circuit and may be actuated either individually or in combination. The sources may also be operated in desiccate only, fulgurate only and cut only modes of operation. The different modes of operation may be selected from a hand-held electrosurgical instrument. An insulated, split patient electrode may be used with the generator where the operating frequency of the desiccate source may be higher than that of the fulgurate or cut sources. A spark detection circuit may also be employed (a) to ensure fulguration when the active electrode is a needle, (b) to prevent neuromuscular stimulation and (c) to ensure continuity of the patient circuit when fulgurating with low levels of current.

59 Claims, 10 Drawing Figures

MULTIPLE SOURCE ELECTROSURGICAL GENERATOR

CROSS-REFERENCE TO RELATED APPLICATION

This application is related to U.S. application Ser. No. 852,431, filed Nov. 17, 1977 by the present applicant and entitled "Contact Area Measurement Apparatus and Method For Use In Electrosurgery and Cryosurgery". This application and the related application are assigned to the same assignee, the related application being incorporated herein by reference.

BACKGROUND OF THE INVENTION

This invention relates to electrosurgery and in particular to an improved electrosurgical generator.

In electrosurgery there are three effects which may be produced by passing radio frequency current through tissue—namely, desiccation, cutting and fulguration. In desiccation, the active electrode is held in firm contact with the tissue with the current passing directly into the tissue and the heating effect being brought about by $I^2R$ heating. Thus, the mode of operation is ohmic. A generator designed for desiccation should be able to pass at least one ampere through 100 ohms.

In cutting, the active electrode is not in good contact with the tissue and electric sparks jump from the electrode to the tissue. The voltage waveform used is generally a sinewave and the sparks are short in length but heat the tissue intensely. The cells burst into steam and the steam maintains the layer of gas between the electrode and the tissue as the incision proceeds. In order to produce a cutting effect without desiccation, the generator must be current limited to less than about 200 milliamperes. Since the open circuit voltage must be high to make a spark, the output impedance must be high, about 3000 ohms. About 100 watts power is sufficient.

In fulguration, the coagulation occurs by means of a high voltage spark which jumps from the active electrode to the tissue. Thus, an arcing mode of operation occurs in both cutting and fulguration. The spark produces intense heating at every point it strikes, but a high crest factor voltage waveform, called a COAG waveform, makes long sparks and distributes the spark widely. This keeps the energy density down and minimizes the cutting effect. A generator designed for fulguration without cutting or desiccation effects needs a very high output impedance, say 5000 ohms or more and should be current limited to less than 200 milliamperes. About 125 watts is adequate.

Figure 1:
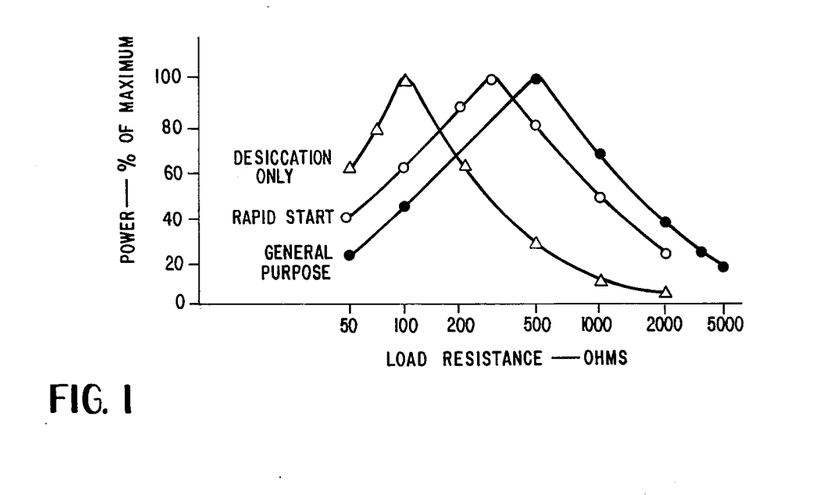
FIG. 1 is a graph of generator output impedance characteristics of known electrosurgical generators.

At present, some general purpose generators have high power at the low impedances, around 100 ohms and similar amounts at high impedances, 3000 to 5000 ohms. In order to achieve this, some generators operate most efficiently into a 400 or 500 ohm resistance, see FIG. 1, General purpose curve. In order to provide the necessary power at low and high impedances, the generator is excessively powerful at 500 ohms. 400 or more watts are required. Desiccation and fulguration or cutting cannot occur simultaneously, so no more than 125 watts is needed at any one instant.

It is thus a primary object of this invention to provide an improved multiple source, electrosurgical generator having at least a separate desiccation source and a separate source for fulguration and cutting where separate sources may also be respectively provided for cutting and fulguration.

It is to be understood the foregoing generator of this invention is different from those prior art generators such as those disclosed in U.S. Pat. Nos. 1,945,867 and 3,058,470 where a spark gap generator (for fulguration) is connected to the same output as a cutting waveform generator. Thus, both of the foregoing modes of operation (fulguration and cutting) are arcing modes in contradistinction to the generator of the present invention where one of the sources operates in and may be optimized for an ohmic mode of operation (desiccation) while the other source operates in and may be optimized for an arcing mode of operation (cutting or fulguration).

By controlling the voltage across the load (tissue) and the current through it, it is possible to confine the electrosurgical effects (arcing or ohmic mode) to whatever is desired. There are known ways to do this and the following attempts to summarize what has been done. At present there are at least four basic, commercially available, output impedance characteristics. These four characteristics accentuate the transfer of power to different regions of the impedance spectrum to enhance different performance. A typical general purpose generator, as discussed hereinabove, may have an output impedance of 500 ohms. This impedance is mainly a function of the number of turns on the secondary winding of the output transformer. The characteristic is rather sharp, that is, it peaks at 500 ohms and falls off rapidly at impedances either above or below that figure. By using low output power settings, and pressing the active electrode against the tissue, it is possible to stay in the desiccation mode and avoid cutting or fulguration. By using higher settings and holding the electrode just off the tissue, one can achieve cutting or fulguration depending on waveform.

In most electrosurgery, desiccation is combined with cutting or fulguration because the surgeon usually starts his cut or fulguration with the electrode in firm contact with the tissue. Since, by definition, the starting mode is desiccation, the desiccation must be complete before the tissue in contact with the electrode will acquire a high enough resistance so that sparking can begin and cutting or fulguration will occur. Thus, for example, in many cutting applications, the cutting electrode must be pressed against the tissue before activating the generator. As a result, the electrode tends to desiccate instead of cut and the surgeon sees this as a delay or a lag. To overcome this, some generators use a "rapid start" characteristic which means fewer turns on the secondary so that the peak power point is at about 250 ohms, see Rapid Start curve of FIG. 1. This characteristic provides additional power to the desiccation part of the spectrum so that the electrode is rapidly driven into high impedances and will begin to spark and cut. The drawback of this characteristic for general use is that the open circuit voltage is reduced and fulguration from a distance is degraded.

For neurosurgery and other applications, it is desirable to have an output that will desiccate only, without any possibility of fulguration or cutting. A low impedance output winding with a peak power at about 100 ohms accomplishes this, see the Microbipolar curve of FIG. 2 and the Desiccation Only curve of FIG. 1.

Figure 2:
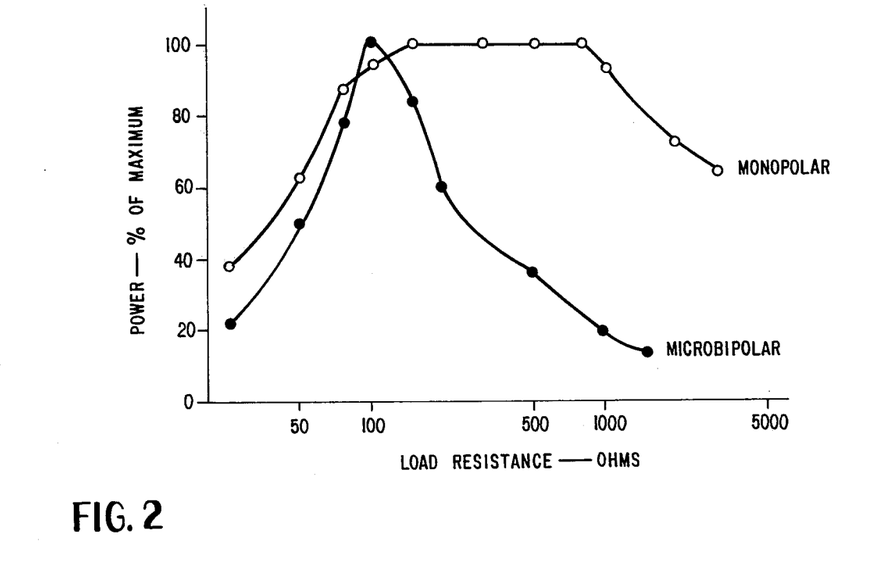
FIG. 2 is a graph of output impedance characteristics of other known electrosurgical generators.

A recently available characteristic is a more flat general purpose characteristic which, instead of peaking at 500 ohms, is flat from about 100 to 1000 ohms, see the Monopolar curve of FIG. 2. This characteristic combines most of the advantages of the standard 500 ohm peak characteristic with the "rapid start". It may be effected by a feedback loop and a voltage clamp which regulate the voltage and current in the output transistors.

At present, a generator which is optimized for all three functions, desiccation, cutting and fulguration, must use at least two secondary transformer windings and, without switching very high voltages, it is not practical to have all three capabilities available with the same hand-held electrode simultaneously.

It is thus a further primary object of the present invention to provide an electrosurgical generator of the foregoing type wherever the different modes (ohmic or arcing) of operation may be optimized and may be effected in a common output circuit whereby all modes are readily available from a hand-held switching, electrosurgical instrument having a plurality of switching positions to permit the surgeon to readily select the desired mode or combination of modes of operation.

As stated above there are certain applications where a desiccation only mode of operation is desirable such as in neurosurgery. Further, there are applications where a fulguration only or cutting only is desired. Thus, for example, one practical application of fulguration-only is in the fulguration of bleeding gastrointestinal ulcers. This procedure is done through an endoscope and because the wall of the stomach or bowel is very thin, it is desirable that the coagulation necrosis be confined to the surface of the tissue. Because desiccation causes deep coagulation necrosis and the depth and effectiveness are very dependent on the pressure one exerts on the electrode, controlling this pressure through an endoscope is very difficult. Fulguration provides very consistent, shallow necrosis with rigid crust that can stop even very large arterial bleeders. This works well, but if the electrode inadvertently touches the wall of the bowel, desiccation may occur and deep necrosis may result. By limiting the coagulation to fulguration, this possibility is avoided and the technique requires less skill to perform.

It is thus a further primary object of this invention to provide improved electrosurgical generators which operate in a desiccate only mode of operation or a fulgurate only or cut only mode of operation.

It is a further object to provide a multiple source generator of the type described hereinbefore where one of the sources operates in a desiccate only mode and at least one of the sources operates in an arc (fulguration or cutting) only mode.

As stated above, a fulgurate only (no desiccation) characteristic is desirable in some applications. However, as also indicated hereinbefore, some desiccation is needed to initiate the establishment of the arc required for fulguration. Further, as in some instances a "rapid start" cutting action is desired.

Hence, it is a further object of this invention to provide an improved multiple source generator of the aforesaid type where a desiccate only source and a cut only and/or fulgurate only source(s) are independently adjustable whereby the desiccate power level can be adjusted with respect to the cut only or fulgurate only power level to provide sufficient desiccation to initiate the requisite arc either with a slight delay or on a "rapid" start basis. Prior art electrosurgical generators are known wherein control of the generator output is effected in accordance with sensed tissue impedance. Thus, in British Pat. No. 855,459 there is disclosed a voltage feedback circuit which turns the generator off when a predetermined level of "coagulation" of the tissues has occurred, the coagulation possibly being due to desiccation as opposed to fulguration. Hence, there may be disclosed in the British Patent a desiccation only circuit using voltage feedback. It is also known as described in U.S. Pat. Nos. 3,923,063 and 4,024,467 to vary the duty cycle of the applied signal by a voltage feedback circuit to prevent cutting during coagulation, which does not correspond to the prevention of desiccation. Also in U.S. Pat. No. 3,601,126 there is disclosed a current feedback circuit for regulating the output power of an electrosurgical generator. However, in none of the foregoing patents is there disclosed an arc (cut or fulgurate) only mode of operation or the combination of desiccate only and arc (cut or fulgurate) only modes of operation discussed hereinabove. Further, as will be described hereinafter, it has been empirically determined in accordance with the present invention that positive current feedback is effective for implementing a desiccate only mode of operation.

Thus, further objects of this invention are (1) to provide an arc only mode of operation and (2) to employ positive current feedback to implement a desiccate only mode.

Another factor relating to multiple source generators is discussed in my copending application entitled "Patient Contact Area Measurement Apparatus and Method For Use In Electrosurgery and Cryosurgery" filed Nov. 17, 1977. In this application is described a capacitive, split patient electrode which, together with the patient electrode cable may comprise a resonant circuit to minimize the voltage between patient and ground where the split patient electrode comprises a pair of separated plates both of which are connected to an electrosurgical generator via the patient electrode cable, there being disposed on the plates a dielectric layer adapted for contact with the patient. In the capacitive split patient electrode patent application, it is stated the dielectric has to typically withstand 5000 volts and the electrode has to be a relatively small size so the capacitance could not be very large, typically 3000 to 4000 pF. As a result, the operating frequency has to be high to pass large desiccation currents. Otherwise, large voltages would appear between the patient and ground. Even with the patient electrode and cable resonating at the operating frequency, it has been found the application of the patient electrode becomes quite critical when an attempt is made to resonate the cable at low frequencies, say 750 KHz. At 2.2 MHz, for example, however, the application is not critical and patient contact area typically in excess of 60% provides a sufficiently low patient to ground impedance.

From the foregoing it can be seen the higher operating frequency of 2.2 MHz is desirable when using an insulated (dielectric) electrode to permit effective handling of the larger current associated with the desiccation (ohmic) mode of operation. Smaller currents are associated with cutting and fulguration (arcing) modes of operation and thus the problem of a high potential between the patient and ground is not as significant. Hence, cutting and fulguration can occur at a lower frequency of operation.

Thus, it is a further object of this invention to provide an electrosurgical generator having separate sources of the above type where a higher frequency of operation is employed for desiccation to thereby permit the use of an insulated, capacitive electrode which may be of the split type.

As discussed hereinbefore, a fulguration only mode of operation is desirable in certain applications whereby the patient current is limited to a predetermined value such as 200 ma. to thereby prevent desiccation. However, in some applications, it is desirable to employ needle electrodes in the fulguration only mode of operation. The current density through such a needle electrode is quite high due to the small contact area thereof with the treated tissue. Hence, the current should be limited to a value even less than 200 milliamperes in these applications.

In accordance with a further object of this invention, improved electrosurgical circuitry is provided for ensuring a fulguration only mode of operation even when a needle electrode is employed. In order to effect the foregoing, spark detection circuitry is employed in a preferred embodiment of this invention to detect the presence of sparking.

The foregoing spark detection circuitry is useful in other applications. The operation of the spark detection circuitry of this invention relies upon the stochastic nature of the sparking phenomenon. In particular, the very low frequency portion of the spectrum is detected in accordance with a further object of this invention, the low frequencies corresponding to those capable of producing neuromuscular stimulation or even shock or fibrillation. Spark detection circuitry and techniques are disclosed in U.S. Pat. Nos. 3,163,165 and 3,515,943, German Pat. No. 2,504,280 and French Pat. No. 1,275,415. However, none of the foregoing patents include circuitry sensitive only to the low frequency portion of the sparking spectrum.

In accordance with a further object of this invention, the aforesaid spark detection circuitry may also be employed to detect lack of circuit continuity in the patient circuit during fulguration (or cutting) mode of operation where the current is very low. This is in contradistinction to the process disclosed in U.S. Pat. No. 3,812,858 which simply discloses circuitry for sensing lack of power in the patient lead, the circuitry being insensitive to whether fulguration (or cutting) is occurring.

Other objects and advantages of this invention will be apparent from a reading of the following specification and claims taken with the drawing.

DETAILED DESCRIPTION OF THE PREFERRED EMBODIMENTS OF THE INVENTION

In the drawing like reference numerals refer to like parts.

Figure 3:
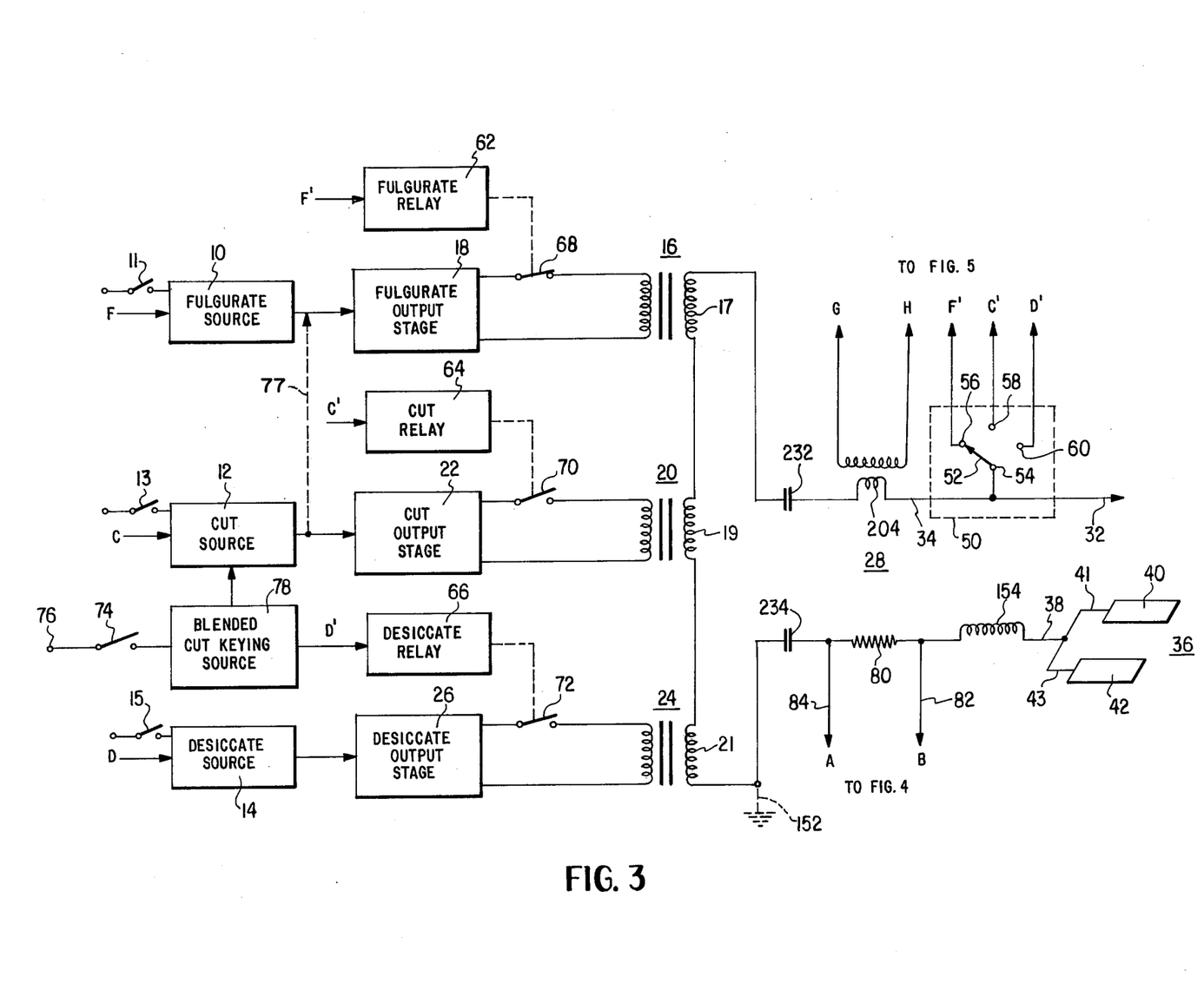
FIGS. 3 and 4 are a combined block and circuit diagram of an illustrative triple source generator in accordance with the invention.
Figure 4:
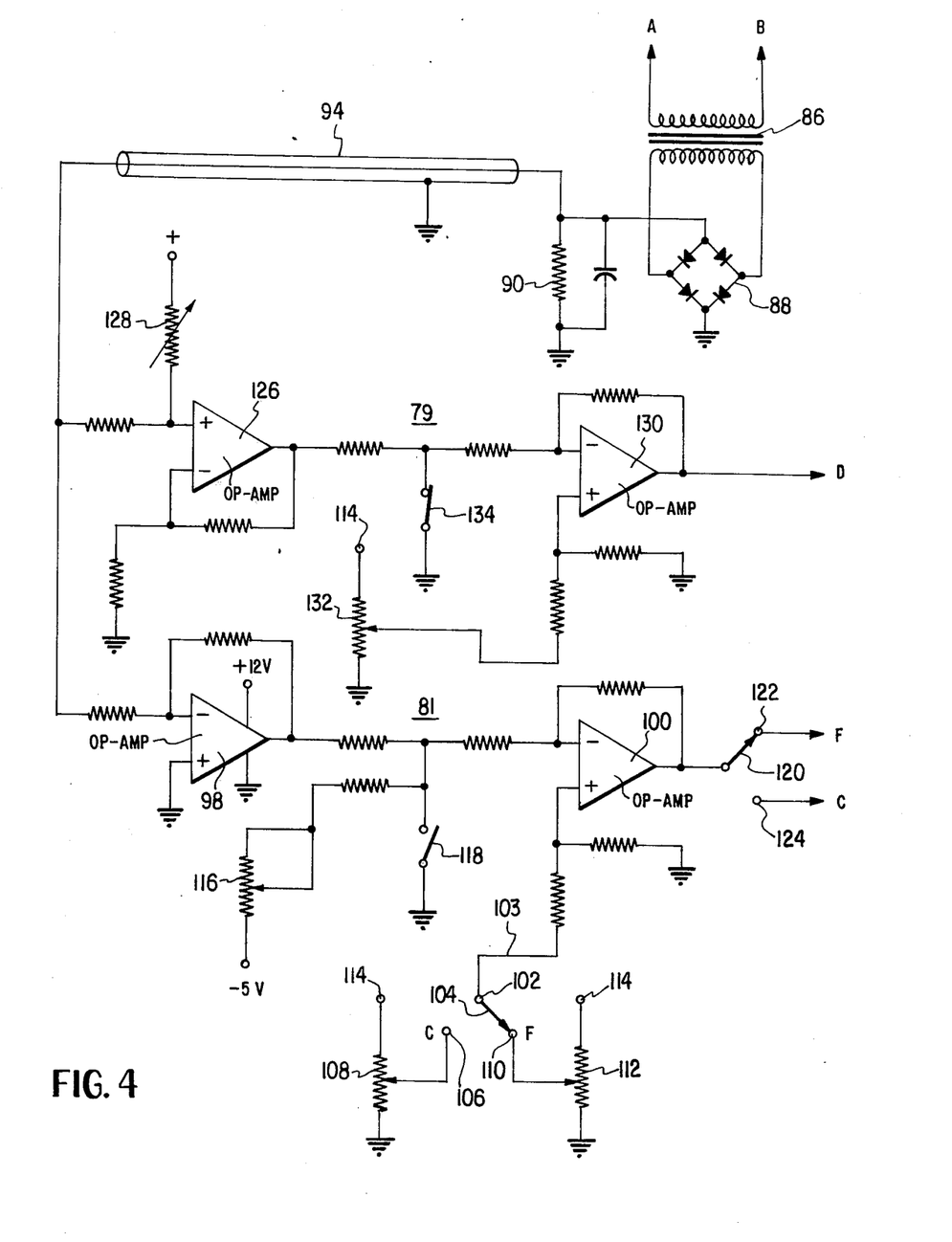

Referring to FIGS. 3 and 4, there is shown an illustrative embodiment of a triple source electrosurgical generator in accordance with the present invention where a fulgurate source 10 which may be actuated by a switch 11, a cut source 12 which may be actuated by a switch 13, and a desiccate source 14 which may be actuated by a switch 15. Fulgurate source 10 is connected to a transformer 16 through a fulgurate power amplification output stage 18 while cut source 12 is connected to a transformer 20 through cut power amplification output stage 22 and desiccate source 14 is connected to a transformer 24 through a desiccate power amplification output stage 26. Transformers 16, 20 and 24 are all coupled to a common output circuit generally indicated at 28, which includes secondary windings 17, 19 and 21, the latter being connected in series. It should be understood other common output circuit configurations may also be used. Secondary winding 17 is connected to an active electrode 32 via an active cable or lead 34 and winding 21 is connected to a split patient electrode generally indicated at 36 via a patient cable or lead 38. Split patient electrode 36 comprises patient plates 40 and 42, a peferred embodiment of which will be described in more detail hereinafter with respect to FIGS. 5 and 5A. The fulgurate source may typically comprise a high crest factor, 750 KHz, 200 ma., current source capable of delivering 125 watts into a 5000 ohm load (patient tissue), the cut source may typically comprise a sinewave 750 KHz, 200 ma. current source capable of delivering 100 watts into a 3000 ohm load and the desiccate source may typically comprise a sine-wave, 2.2 MHz. voltage source capable of delivering 1 ampere into a 100 ohm load.

Figure 5:
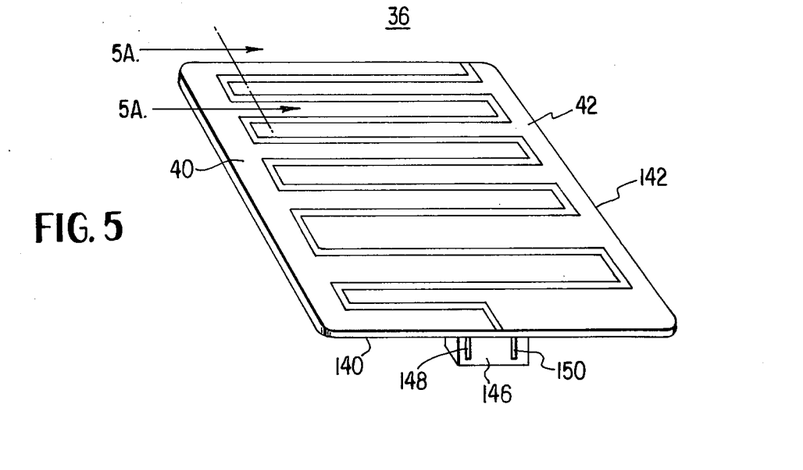
FIG. 5 is a diagrammatic, perspective view of an illustrative split patient electrode for use with the circuitry of FIG. 3.

Thus, the sources 10-14 are connected either individually or in combination to common output circuit 28 to energize active electrode 32 depending upon which source(s) is actuated. As will be brought out in detail hereinafter, when split patient electrode 36 is of an insulating type as shown in FIG. 5, it is desirable to operate the desiccate voltage source at a higher frequency than the fulgurate and cut sources where the desiccate source would typically be at 2.2 MHz and the fulgurate and cut sources would typically be at 750 KHz.

In accordance with one aspect of the invention, it is possible to switch between sources 10–14 at a hand-held electrosurgical instrument 50 without having to switch high voltages, which, for example, would appear across secondary winding 28. Thus, instrument 50 includes a single pole, triple throw switch 52 which permits the surgeon to manually select the desired mode of operation. The common terminal 54 of switch 52 is connected to active lead 34 and the armature thereof is selectively setable to terminals 56-60 which are associated with a fulgurate relay 62, a cut relay 64 and a desiccate relay 66 via appropriate circuitry for isolating the relays from the radio frequency operating current in lead 34. Appropriate isolating circuitry is described in U.S. Pat. Nos. 3,699,967 and 3,801,800, both of which are hereby incorporated herein by reference. Thus, referring to block 20 of FIG. 3 of Pat. 3,699,967 or block 11 of Pat. 3,801,800, there are shown single pole, double throw switches for selecting either cut or coagulate (fulgurate) modes of operation. The foregoing single pole, double throw switches correspond to single pole, triple throw switches 52 of the present invention where switch 52 simply incorporates additional terminal 60 to permit separate selection of the desiccate mode of operation.

It is also possible to implement the selection of three modes of operation at instrument 50 without having to employ the additional terminal 60. Thus, two switches (not shown) are provided at instrument 50 where closure of the first switch connects active lead 34 to terminal 56, closure of the second switch connects lead 34 to terminal 58 while closure of both switches connects lead 34 to both of the terminals 56 and 58. Simple logic (not shown) at the generator then determines whether the fulgurate, cut or desiccate mode of operation has been selected.

Relays 62-66 respectively actuate contacts 68-72, the contacts isolating their respective output stages from the other sources when they are open. Alternatively, the contacts can be disposed at lower voltage points such as, between source 10 and output stage 18 to thereby permit switching of lower voltages. In addition to the selection of the modes of operation by switch 52, a blended cut mode of operation can also be selected by a panel switch 74 which connects an appropriate voltage source 76 to blended cut keying source 78 for energization of source 12.

Of course, actuation of sources 10, 12 and 14 may be effected by other conventional means such as panel switches 11, 13 and 15 or a footswitch whereby the various modes of operation may be either effected individually or in combination. Thus, to produce a cut with a desiccation start, both cut source 12 and desiccation source 14 are activated. Since the power levels of each mode are independent, it is easy to produce a so-called "rapid start" by setting the desiccation level relatively high in comparison to the cut level. Blended cutting may be produced by keying cut source 12 on and off by source 78 at a repetition rate and duty cycle that produces the desired crest factor. This will produce a satisfactory blended cut up to a crest factor of about 5. If a desiccation start is desired, then the desiccation mode is keyed continuously while cut source 12 is being keyed on and off. Since crest factor is defined as the ratio of peak voltage to RMS voltage of a waveform, the higher the crest factor, the less tendency the waveform has to produce a cutting effect. Thus, the addition of the desiccation waveform decreases the crest factor, but because the desiccation voltage is incapable of making sparks it does not change the effective crest factor.

In order to obtain desiccation and a sparking mode (cutting or fulguration) from a common output circuit, at least one feedback circuit should be used to alter the basic output characteristic of the uncontrolled transformer outputs. Further, in order to limit (1) the current passing through the patient during the fulguration or cut modes of operation and thereby prevent desiccation during these arcing (or sparking) modes or (2) the voltage applied to the patient during the desiccation mode and thereby prevent arcing during this ohmic mode, desiccate only and arc only feedback circuits generally indicated at 79 and 81 in FIG. 4 may be employed in the following manner. The current in patient lead 38 (FIG. 3) is sensed by a small resistor 80 serially inserted in patient lead 38. The value of this resistor is typically approximately 0.1 ohms. Leads 82 and 84 connected across resistor 80 are connected to a voltage transformer 86 (FIG. 4) which isolates the current feedback signal from the RF output. Thus, a voltage signal proportional to the current is transferred to ground without compromising the RF isolation of the output circuit. This small RF signal is applied to a fullwave rectifier 88, the output of the rectifier being smoothed by filter 90. The rectified voltage is then applied to operational amplifiers 98 and 126. Switch 118 which may be on the console panel determines whether the arc only mode is selected while switch 134 determines whether the desiccation only mode is selected. If switch 118 is open, the fulgurate only or cut only mode is selected depending on which one of the sources 10 or 12 is activated. If switch 134 is open, the desiccate only mode is selected while if both switches 118 and 134 are open, both modes are selected as discussed above. Assuming the switch 118 is open as shown in FIG. 4 so that an arcing mode has been selected, the voltage fed back from filter 90 is applied to the inverting input of operational amplifier 98 which in turn is connected to an operational amplifier 100. Applied to the non-inverting input of operational amplifier 100 over line 103 is the common terminal 202 of a single pole, double throw switch 104. The terminal 106 of switch 104 is connected to a cut potentiometer 108 while the terminal 110 is connected to a fulgurate potentiometer 112 where potentiometers 108 and 112 are connected between reference voltage source 114 and ground. The purpose of potentiometers 108 and 112 is to respectively control the level of the cut and fulgurate waveforms applied to the patient. The purpose of the feedback voltage at the output of amplifier 98 is to decrease the control voltages developed by potentiometers 108 and 112 in accordance with the sensed current passing through the patient. The sensitivity of operational amplifier 100 is regulated by potentiometer 116. Note switch 118 may also be under the control of switch 52 and would be open whenever switch 52 contacts either terminal 56 or 58 to indicate an arcing mode of operation. The output of operational amplifier 100 is applied to a single pole, double throw switch 120, the output terminals 122 and 124 of which are respectively connected to sources 10 and 12 of FIG. 3. Hence, as will be described in more detail hereinafter, the outputs of switch 120 may be employed to regulate the output power of sources 10 and 12. As can be seen from the foregoing, negative current feedback is employed to limit the current in the arcing modes of operation and to thereby prevent desiccation in these modes of operation where the response time of the feedback circuit should be at least less than 10 milliseconds (ms) and preferably less than 1 ms to avoid significant desiccation immediately after the active electrode 32 contacts the patient's tissue. Alternatively, positive voltage feedback could also be employed to effect the desired current limiting although such a feedback arrangement is not preferred because of the tendency for the system to oscillate.

In the desiccation only mode of operation it is desirable to limit the applied voltage and thereby prevent sparking to the patient tissue. This is particularly the case in many neurosurgical procedures. In accordance with this invention, a positive current feedback is employed whereby the output voltage from filter 90 is applied to the non-inverting terminal of operational amplifier 126. Operational amplifier 126 has a small positive bias adjusted by a variable resistor 128. When switch 134 is open, the output of amplifier 126 is connected to the inverting input of an operational amplifier 130. A desiccation potentiometer 132 is connected to the non-inverting input thereof to set the basic desiccation power level. The output of comparator amplifier 130 is connected to desiccation source 14 of FIG. 3. If potentiometer 132 were allowed to drive source 14 directly, without feedback, the generator would desiccate first then transfer quickly into fulguration, for example. By placing operational amplifier 130 in series with the potentiometer, the feedback can determine what percent of the original potentiometer level is actually passed along to drive output stage 26. To achieve a desiccation only characteristic, the output of operational amplifier 130 must be held very low when the current is low where the response time of the feedback circuit should be at least less than 10 ms and preferably less than 1 ms. If the gated feedback is applied to the amplifier in a positive sense, then a little current flow will cause more current to flow until the full level of potentiometer 132 is reached. The sensitivity of the feedback must be set by variable resistor 128 so that this can only occur during desiccation. When the desiccation is complete, the current will drop very suddenly and the output voltage will rise. This is detected by the feedback loop and the current is returned to its original state so that the output of amplifier 130 is held very low. Thus, the voltage applied to the patient from active electrode 32 will accordingly be reduced to a level where sparking cannot occur. A switch 134 is also connected to the output of amplifier 126 and this switch may be either manually opened or opened in response to switch 52 being connected to terminal 60 whenever desiccation is required.

The foregoing desiccate only effect can also be achieved with negative voltage feedback. That is, the output of amplifier 130 can be turned down when the voltage across the tissue rises. Amplifiers have been built which worked on both principles. Empirically, it was found the current feedback approach worked better and was easier to build. Voltage feedback has the advantage that it is a negative feedback and thus is stable and has no tendency to oscillate.

The above discussed fulgurate only or cut only modes of operation are effected by reversing the sense of the feedback input whereby the current is limited instead of the voltage. This means that if the active electrode is pressed firmly against the tissue, there is no visible effect because the current that does flow serves to change the output of amplifier 100 to a low level. As soon as the active electrode is released from contact with the tissue, the output of amplifier 100 is allowed to rise to the basic, programmed level established by either potentiometer 108 or 112 and fulguration or cutting commences, depending on the generator voltage waveform selected.

One practical application of fulguration only is in fulguration of bleeding gastrointestinal ulcers. This procedure is done through an endoscope and because the wall of the stomach or bowel is very thin, it is desirable that the coagulation necrosis be confined to the surface of the tissue. Because desiccation causes deep necrosis and the depth and effectiveness are very dependent on the pressure one exerts on the electrode, controlling this pressure through an endoscope is very difficult. Fulguration provides very consistent, shallow necrosis with a rigid crust that can stop even very large arterial bleeders. This works well, but if the electrode inadvertently touches the wall of the bowel, desiccation may occur and deep necrosis may result. By limiting the coagulation to fulguration, this possibility is avoided and the technique requires less skill to perform. In a prototype generator that was built, this feature was activated by means of switch 118 on the front panel which ungrounded the negative input to gated amplifier 100 thus allowing the program level input from potentiometer 108 or 112 to be controlled by the feedback.

Fulguration source 10 may be as described in U.S. Pat. No. 3,963,030 granted to D. Newton which is hereby incorporated herein by reference. Thus, the feedback circuitry of FIG. 4 would be such that the width of the inductor charging current pulses from the generator disclosed in Pat. No. 3,963,030 would be controlled in accordance with the amount of negative current feedback from amplifier 98 to thereby maintain the average patient current below a predetermined minimum such as 200 ma. In particular, potentiometer 88 of FIG. 4 of Pat. 3,963,030 corresponds to potentiometer 112 of the present invention. The output of potentiometer 88 would be connected through switch 104 to the non-inverting input of operational amplifier 100 of the present invention while the output of operational amplifier 100 would be connected to the anode of diode 91 of FIG. 4 of U.S. Pat. 3,963,030 whereby the desired pulse width control would be effected in response to the feedback current from operational amplifier 98 of the present invention.

Alternatively, the amplitude of the bursts can be controlled directly. Thus, in the above-mentioned U.S. Pat. No. 3,699,967 the output of operational amplifier 100 of the present invention may be used to change the position of the tap of potentiometer R30 in FIG. 4 of Pat. 3,699,967 via a servomechanism (not shown) whereby the amplitude of the fulgurate bursts would be controlled in accordance with the amount of feedback from operational amplifier 98 of the present invention.

The cut current source 12 may correspond to the cut current source of U.S. Pat. No. 3,699,967 corresponding to the astable multivibrator of FIG. 4 thereof. In order to regulate the output of the multivibrator in accordance with the feedback output from operational amplifier 98 of the present invention, the position of the tap of potentiometer R31 of Pat. 3,699,967 may be changed via a servomechanism by the output of operational amplifier 100 of the present invention.

In order to implement the blended cut keying source 78 and associated switch 74 of FIG. 3, the switch 74 may correspond to switch S2 of U.S. Pat. No. 3,699,967 and source 78 may correspond to the circuitry controlled by switch S2.

It is also within the scope of the present invention to utilize a common transformer for the fulgurate and cut current sources as indicated by the dotted line 77 in FIG. 3. Thus, for example, the common cut/fulgurate source disclosed in above Pat. 3,699,967 may be used where transformer T2 of FIG. 3 thereof would take the place of transformers 16 and 20 of FIG. 3 of the present invention. The terminals 56 and 60 of FIG. 3 of the present invention would then correspond to terminals B5 and B6 of FIG. 5 of Pat. 3,699,967. Thus, there would be two transformers, one corresponding to the common fulgurate/cut transformer and the other to transformer 24. Except for the elimination of secondary winding 19, the output circuitry connected thereto would remain unchanged.

Figure 5A:
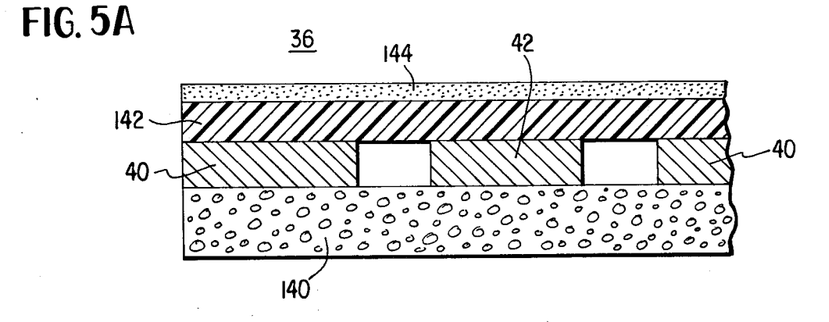
FIG. 5A is a partial cross-sectional view taken along the line 5A—5A of FIG. 5.

Referring to FIG. 5, there is shown a perspective, diagrammatic view of a capacitive, split patient electrode corresponding to split electrode 36 of FIG. 3 where FIG. 5A is a partial cross-sectional view taken on the line 5A—5A of FIG. 5, the foregoing split electrode being described and claimed in the aforesaid copending application entitled "Patient Contact Area Measurement Apparatus and Method For Use In Electrosurgery and Cryosurgery". A foam backing pad 140 has disposed thereon a pair of interdigitated foil electrodes 40 and 42, the interdigitation enhancing the overlap of the electrodes. Disposed on the electrodes is a dielectric insulating layer 142 which in turn is provided with an adhesive coating 144. A two conductor connector 146 is provided at the underside of backing pad 140. The connector includes prongs 148 and 150 which respectively engage electrodes 40 and 42 and which are respectively connected to wires 41 and 43 of FIG. 3. Dielectric layer 142 should be thick enough to prevent dielectric breakdown if contacted by the activated active electrode. Thus, the dielectric layer should typically be able to withstand about 5000 volts. A layer of Mylar at least 0.005 inches thick would be satisfactory.

In lieu of a split insulative patient electrode, there may also be employed a unitary insulative electrode which is not split. That is, the construction of the electrode would correspond to that disclosed in FIG. 5 except that a single electrode would be connected to the patient cable 38 as is conventional. Unitary, insulative electrodes are known. In general, insulative patient electrodes are advantageous when compared to conventional, gelled patient electrodes in terms of ease of manufacture, storage, and application. However, a difficulty with a capacitive (or insulative) patient electrode is that the dielectric insulating layer 142 must be fairly thick to prevent breakdown by the high voltage available from the generator. If, as stated above, a Mylar layer at least 0.005 inches thick is employed, the insulation is adequate, but the plate must be quite large to prevent potentially dangerous voltages from occurring between the cable and the patient's skin. This is especially important if the patient side of the generator output circuit is ground referenced. If the generator is well isolated, it is not as important. A typical patient return electrode of the gelled ("stick-on") design is relatively small—that is, about 9 by 6 inches. An insulating layer of 0.005" Mylar plus adhesive on a foil electrode of this size yields a capacitance of about 4000 pf to skin at radio frequencies for the capacitive split electrode of FIG. 5. If the voltage between the patient's body and ground is to be kept below 30 volts RMS, for example, the current will be limited to about 0.57 amperes at 500 KHz. This is adequate for cutting or fulguration, but it is not adequate for desiccation. For desiccation a current of at least 1 ampere RMS is needed so higher frequencies must be used. Of course, the foregoing is readily accommodated in the present invention since fulgurate and cut sources 10 and 12 may be operated at a lower frequency (say, 750 KHz. to thereby lessen leakage from active lead 34) while desiccation source 14 may be operated at 2.2 MHz. to thereby facilitate the use of a capacitive patient electrode.

If it is assumed the generator output of FIG. 3 is grounded as indicated in dotted lines at 152 (although the generator output is typically isolated from ground), one of the difficulties encountered with such a high frequency, grounded generator is that the inductance of cable 38 connecting patient electrode 36 to the generator is significant and the voltage drop across this inductance can cause currents to seek other paths to ground via current division. These other current paths could be at small, grounded contact points on the patient's skin and are a threat to the patient. The inductance of a 10 foot cable is about three microhenries. At 2 MHz one ampere of current flowing through this inductance can generate a voltage of about 40 volts. In contrast, the impedance of the insulated split patient plate of FIG. 5 drops with frequency and thus the patient cable and the split capacitive electrode comprise a series resonance L-C circuit. With a 4000 pf electrode and a typical ten foot, two-wire cable, the resonance occurs at about 2 MHz. Experiments have shown that the Q of this resonance point is such that an electrode 36 which is not perfectly applied, say only 80% contact, still has an acceptably low impedance to ground.

The return fault ground monitor described in copending U.S. application Ser. No. 721,821, filed Sept. 9, 1976 by D. Newton, et al. (the foregoing being incorporated herein by reference) works well with the foregoing resonant system because the return fault circuit measures ground currents which are a threat to the patient. If the pad is misapplied, but not necessarily dangerous, the extra voltage to ground will cause currents to flow to ground and these may be detected as a fault by the return fault monitor. On the other hand, if there are no such paths to ground, no ground currents will flow and the return fault system will not detect a fault since there is no actual threat to the patient.

It is also possible to insert an extra inductor 154 (FIG. 3) in series with patient cable 38 and make the capacitive plate 36 resonate at lower operating frequencies. In experiments at 750 KHz the Q of such a system is much higher and thus the patient plate application becomes quite critical. That is, if the capacitive electrode lacks a few percent of being perfectly applied, it will have a very high impedance. On the other hand, if it is perfectly applied, the total impedance between the patient's body and ground can be much lower than can be achieved with a conventional plate and a simple 10 foot cable. This situation makes current division much less likely. Thus the inconvenience of the more critical patient electrode application is partially offset by the diminished likelihood of the return fault circuit being triggered.

It should also be noted that the multiple source generator illustrated in FIGS. 3 and 4 can be implemented in modified embodiments and still effect desiccate only and/or arc only modes of operation. Thus, desiccate only feedback circuit 79 may be eliminated. Note the system of FIGS. 3 and 4 employs feedback circuit 79 to effectively make a high impedance transformer behave as if it were a low impedance. However, since output transformers 16, 20 and 24 are separate, the output impedance of desiccate source 14 can be made low by the prior art technique described hereinbefore—that is, by providing a relatively small number of turns on secondary winding 21. If source 21 operates at 2.2 MHz, the series impedance of secondary windings 17 and 19 should also be low at this frequency. Appropriate filter-type circuitry (not shown) may also be employed to lower the effective impedances of windings 17 and 19. When a sufficiently low output impedance is effected for source 14 in the foregoing manner, the system of FIGS. 3 and 4 minus desiccate only feedback circuit 79 will operate in a desiccate only mode of operation when switch 52 is connected to terminal 60. Connection of the switch to terminal 56 or 58 will switch in an arc only mode of operation where the system would employ arc only feedback circuit 81.

Alternatively, arc only feedback circuit 81 may be eliminated from the FIG. 4 circuit whereby the output impedance(s) of fulgurate and/or cut sources 10 and 12 can be made large by providing a relatively large number of turns on secondary windings 17 and/or 19 to thereby effect an arc only mode of operation when switch 52 is connected to terminals 56 or 58 and a desiccate only mode of operation, which would employ desiccate only feedback circuit 79, when switch 52 is connected to terminal 60. However, it is preferable to employ the feedback circuit 81 to effect the arc only mode of operation.

A further modification would be to employ only cut source 12, for example, and its associated output transformer 20 together with desiccate only feedback circuit 79. Eliminated would be fulgurate source 10 and its associated transformer 16, desiccate source 14 and its transformer 24 and arc only feedback circuit 81. Output transformer 20 would be connected to active and patient leads 34 and 38 in a conventional manner and the output impedance of source 12 would normally be sufficiently high to effect arcing from active electrode 32 to the patient when switch 52 was connected to terminal 58. Upon switching to terminal 60, the desiccate feedback circuit 79 would be switched in to lower the output impedance of source 12 and thereby to limit the voltage on active electrode 32 to a desiccate only value at which arcing from the active electrode is not likely.

Of course, the common output transformer 20 could also be connected to a fulgurate source as discussed hereinbefore whereby a three mode system would be implemented. That is, whenever switch 52 was connected to terminals 56 or 58, an arcing mode of operation would be selected and desiccate only feedback circuit 79 would be out of the system. Switching to terminal 60 would switch circuit 79 into the system and would effect the desiccate only mode described above.

Figure 6:
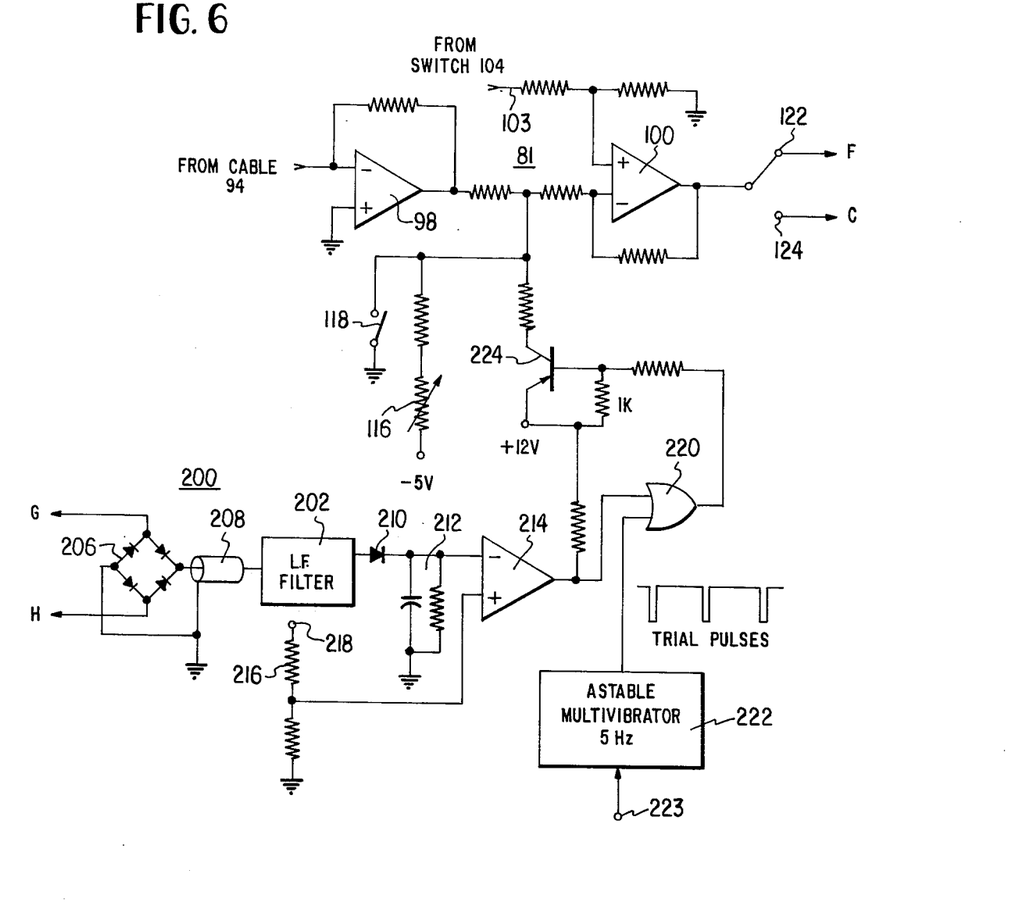
FIG. 6 is a combined block and circuit diagram of illustrative circuitry for implementing a fulguration only (or cutting only) mode of operation with needle tip electrodes.

Reference should now be made to FIG. 6 which is a combined schematic block diagram which illustrates a further embodiment of this invention wherein the generator is operated in a fulgurate only (or cut only) mode of operation wherein the current which passes through the patient is limited to a value which is substantially less than the value to which the current is limited by the negative feedback loop comprising amplifier 98 and operational amplifier 100 of FIG. 4. The circuitry of FIG. 6 is a modification of the above negative feedback loop and it is particularly advantageous when the active electrode comprises a fine needle. The negative feedback circuit of FIG. 4 typically limits the patient current to about 200 ma. For conventional blade electrodes, whose contact area with the patient tissue is about a few square millimeters, the current limited value of 200 ma. is satisfactory since desiccation is at best rather slow. However, there are some applications wherein needle electrodes are required such as the fulgurating of bleeding ulcers through an endoscope. The current density with a needle tip electrode is quite high. Thus, even though the current is no more than 200 ma., the tendency for desiccation to occur is substantial.

In the embodiment of FIG. 6, spark detection circuitry indicated at 200 is uniquely employed in accordance with the present invention to render desiccation virtually impossible even with a needle point electrode. In electrosurgery, fulguration and cutting are effected by radio frequency electric sparks which jump from the active electrode to the tissue. This sparking is a stochastic process since each spark has a different duration. As a result the sparking process produces electrical noise in a continuous spectrum both above and below the primary frequency of the generator. The low frequency portion of the spectrum extends all the way down to DC although the amplitudes of such low frequency currents are quite small. However, these low frequency components can be and are detected by a low pass filter 202 which is shown in further detail in FIG. 7.

The basic purpose of using spark detection circuitry 200 is to detect whether or not fulguration (or cutting) is indeed occurring. If it is not occurring the circuitry of FIG. 6 will limit the patient current to a value an order of magnitude less than 200 milliamperes whereby desiccation cannot occur even if a fine needle tip electrode is contacting the gastrointestinal lining, for example. Hence, coagulation of a bleeding ulcer, for example, by fulguration as opposed to desiccation is assured. Accordingly, a transformer 204 may be provided with its primary winding in series with active cable 34 of FIG. 3. The secondary thereof is connected to terminals G and H of FIG. 6. The transformer 204 may also be disposed in patient cable 38. Transformer 204 is connected to a full wave rectifier 206 which in turn is connected to a coaxial cable 208. The output of cable 208 is applied to filter 202 which passes only the low frequency components of the signal on line 34. The low frequency signal is then rectified by diode 210 and smoothed by filter 212 and applied to the inverting input of an operational amplifier comparator 214. Applied to the non-inverting input of comparator 214 is the output from a voltage divider 216 which is connected to a source of regulated voltage 218, the purpose of voltage divider 216 being to establish a predetermined level which corresponds to the occurrence of an arcing mode of operation. The output of comparator 214 is applied to an OR gate 220. Also connected to OR gate 220 is an astable multivibrator 222 which generates trial pulses as shown in FIG. 6, the pulses typically occurring about five times a second. The output of OR gate 220 is applied to the base of a transistor 224, the collector of which is connected to the inverting input of operational amplifier 100 as are switch 118 and variable resistor 116.

In operation, transistor 224 is normally conducting to turn off operational amplifier 100 whereby the level control signal applied over line 103 from switch 104 of FIG. 4 is so reduced in value that negligible current flows through the patient thereby preventing desiccation at this time even with a needle tip electrode. Each time a trial pulse occurs, the transistor 224 is turned off. Hence, amplifier 100 is turned on and an attempt is made to fulgurate with the current limited to less than 200 ma. RMS. If sparking results, then an output appears from low frequency detector 200 and through OR gate 220 keeps transistor 224 turned off. Of course, as long as fulguration is occurring (a sparking mode of operation), desiccation (an ohmic mode) cannot occur and thus, it is safe for the patient current to be as high as a value slightly less than 200 ma. However, if no sparking occurs during the trial pulse, this may be indicative of the fact that the needle electrode is in firm contact with the tissue to be treated whereby desiccation is attempted with the current possibly being as much as 200 ma. As indicated hereinbefore, if this level current were applied for a long enough period of time, undesirable desiccation could occur. However, the duration of the trial pulses is relatively short (typically less than 0.02 seconds) and the 200 ma. current is not permitted to flow very long if no sparking is detected by detector 200 during the duration of the trial pulse. In particular, if no sparking occurs, there will be no output from comparator 214 to keep transistor 224 turned off after the expiration of the trial pulse. Hence, the output from amplifier 100 will be reduced to the abovementioned low level as soon as transistor 224 turns off. Thus, if the needle electrode remains in contact with the tissue, the desiccation current is limited to the feedback current limit (200 ma. for example) multiplied by the duty cycle of the trial pulse generator, which can be very low. Hence, in this manner, a fulguration only or cut only mode of operation is effectively guaranteed even with needle tip electrodes.

Figure 7:
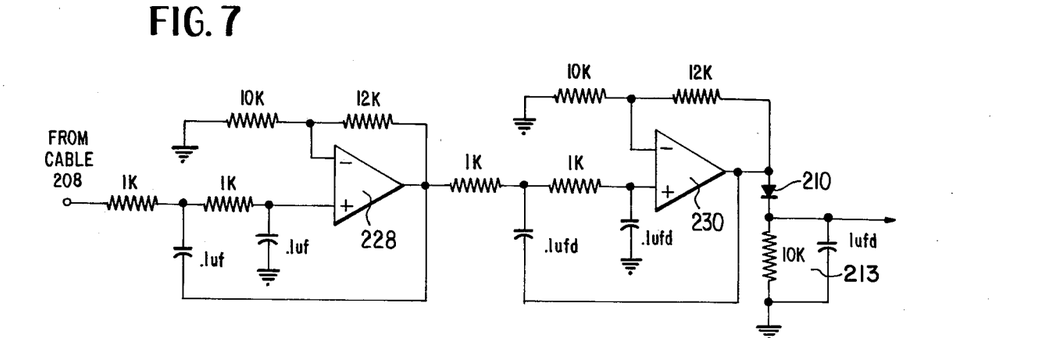
FIG. 7 is a schematic diagram of an illustrative low pass filter for use in the spark detection circuitry of this invention.
Figure 8:
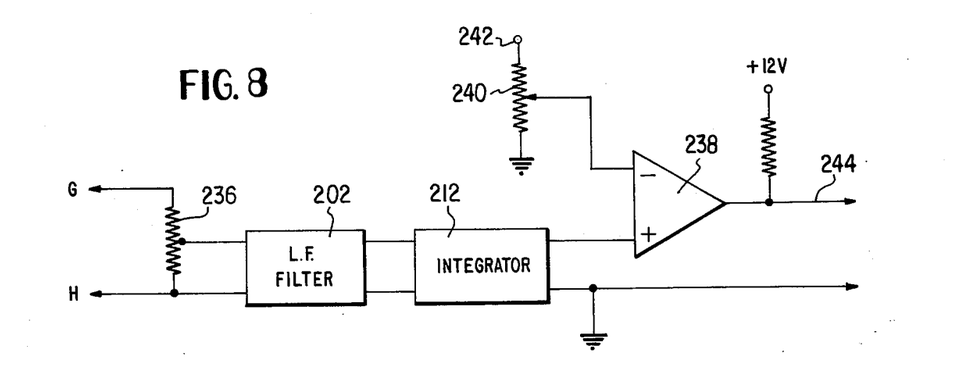
FIG. 8 is a combined block and schematic diagram of a neuromuscular stimulation detector in accordance with the invention.

In FIG. 7 there is shown in further detail the low pass filter 202 which may comprise a standard two stage Butterworth filter amplifier and includes two operational amplifiers 228 and 230. The filter is shielded and together with diode 210 and filter 213 which comprise an envelope detector, a DC level is produced whenever low frequency components of sufficient magnitude are present. In addition to the function performed by the spark detection circuitry 200 of FIG. 6, low pass filter 202 may also be employed in neuromuscular stimulation detector circuitry such as that shown in FIG. 8. In FIG. 3 there is shown a pair of blocking capacitors 232 and 234. Such capacitors are conventionally employed to block the low frequency currents which arise due to the stochastic nature of the spark occurring during either the fulguration or cutting modes of operation. Accordingly, neuromuscular stimulation (and possibly even shock or fibrillation) is prevented. However, if capacitors 232 and 234 were to fail or in the event of a loose connection anywhere in the output circuit, there could be a danger of neuromuscular stimulation. The sparking detector of this invention is unique in that it detects the presence of an arcing mode or operation by detecting the low frequency components which are dangerous insofar as neuromuscular stimulation or fibrillation is concerned. Hence, the G and H terminals of the secondary winding of transformer 204 of FIG. 3 may be connected to a voltage divider 236 (FIG. 8) which in turn is connected to low pass filter 202 and integrator 212. The output of integrator 212 is connected to the non-inverting input of an operational amplifier comparator 238. Connected to the inverting input thereof is a potentiometer 240 which in turn is connected to a regulated voltage supply 242. The purpose of potentiometer 240 is to set the threshold level at which neuromuscular stimulation can occur. When this level is exceeded, comparator 238 will generate an alarm signal on line 244 which may be used either to disable the generator or to flash an alarm.

Figure 9:
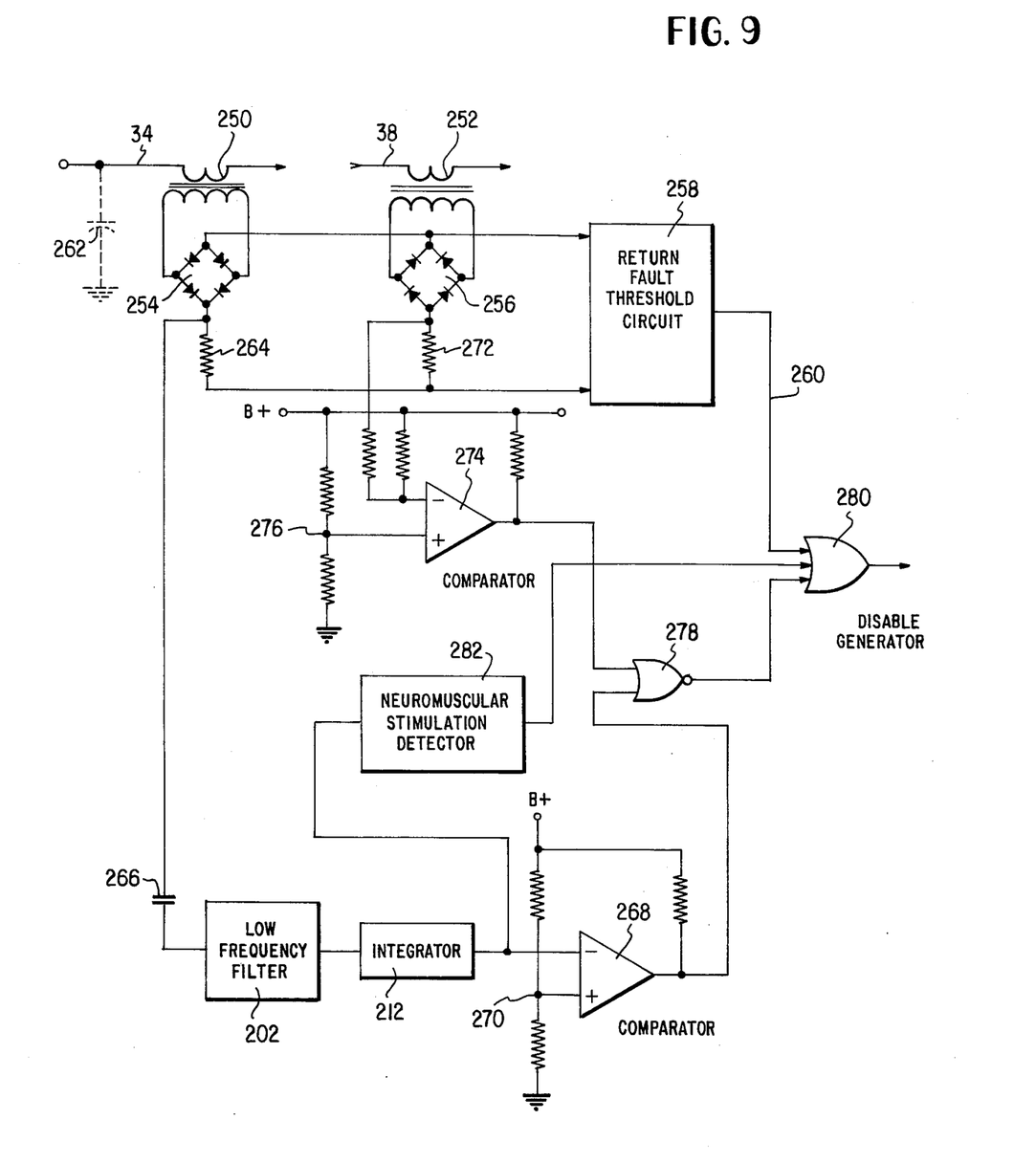
FIG. 9 is a combined block and schematic diagram of illustrative circuitry for detecting the presence of low level currents in the patient return lead during sparking modes of operation.

Another application to which the spark detector of the present invention may be put to is illustrated with respect to FIG. 9. The purpose of this circuitry is to supplement the return fault patient electrode safety system disclosed in the above-mentioned U.S. Patent application Ser. No. 721,821. The return fault safety system is based on the principle that a poor patient return electrode is a threat to the patient because of currents which seek ground via small, grounded contact points which may be touching his skin. The system assumes that any current that does not return to the generator via the patient electrode must be going to ground. Hence, the measurement is made by subtracting the patient lead current from the active lead current to determine the ground current, this being effected by transformers 250 and 252 which respectively sense the current in active and patient leads 34 and 38, rectifiers 254 and 256 which are oppositely poled to subtract DC signals respectively corresponding to the active and patient lead currents and threshold circuit 258 which generates a generator disable signal on line 260 whenever the active lead current exceeds the patient lead current by a predetermined threshold. This system has one major source of error. Because of the coupling between active lead 34 and grounded objects in the operating room (represented by dotted capacitor 262), some of the current reaches ground before it ever reaches the active electrode. This current is not a threat to the patient because the active is referenced to ground and the current stays there once it has bypassed the patient. However, this leakage current is an error because the return fault circuit has no way of knowing whether it entered the patient's body or not.

The coupling between the active and ground is typically 50 or 60 pf and can be as high as 120 pf. The amount of current that can take this path to ground must be allowed for in order for the unit to be compatible with commonly used instruments. It is possible in some applications to fulgurate and cut with current levels that are at the same order of magnitude as these error currents. As a result it is possible to cut and fulgurate without a patient electrode plugged into the generator and without tripping the return fault circuit. There are very few circumstances where this insensitivity presents a real threat to the patient, because the purpose of the return fault circuit is not to prevent surgery at the active electrode. The purpose is to prevent desiccation at small grounded contact points.

Since it is sparking modes at low current levels that are the matter of concern, the lack of a patient electrode can be detected by sensing low level RF currents in patient lead 38. If the low levels of current are not returning through the patient lead, then fulguration is prohibited.

In FIG. 9, fulguration (or cutting) sparking is detected by utilizing a transformer 250 and rectifier 254. The full-wave rectified output is developed across a resistor 264 and applied through capacitor 266 to low pass filter 202 and integrator 212 whereby a DC signal representative of the sparking is applied to the inverting input of an operational amplifier comparator 268. Applied to the non-inverting input is the output from a voltage divider 270, the output of which corresponds to a sparking threshold level. The presence of current returning through patient lead 38 is detected by transformer 252 and rectifier 256, a full-wave rectified output being developed across resistor 272 where the values of resistors 264 and 272 are each typically 100 ohms. The signal across resistor 272 is applied to the inverting input of operational amplifier comparator 274 while applied to the non-inverting input thereof is the output from a voltage divider 276. The voltage divider output corresponds to a threshold which the patient return current must exceed. The outputs of comparators 268 and 274 are applied to a NOR gate 278. When sparking is detected in the output circuit and insufficient current is detected in lead 38, the output from NOR gate 278 is high and is applied to an OR gate 280. Also applied to OR gate 280 over line 260 is the disable output of threshold circuit 258. Further, the neuromuscular stimulation detector of FIG. 8, which is indicated by block 282, may also be connected to OR gate 280 to provide a further condition capable of disabling the generator. The output of OR circuit 280 is applied to appropriate means (not shown) for disabling generators 10 or 12.

With respect to active lead 34 and patient lead 38, the following should also be noted. For purposes of this specification and the following claims, the active lead 34 may be broadly considered to extend from the secondary winding 17 to instrument 50 while the return lead 38 would broadly speaking extend from secondary winding 21 to patient electrodes 40 and 42. Active lead 34 conventionally includes a cable which typically would be 10 foot long and which would be external to a housing for transformers 16-24, capacitor 232 and winding 204. Further, lead 38 may include a cable which also is typically 10 foot long having two wires 41 and 43 in the case of the FIG. 3 embodiment, the cable being external to the aforesaid housing, which would also enclose capacitor 234, resistor 80 and inductor 154. The wires 41 and 43 within the cable would be respectively connected to electrodes 40 and 42.

In summary, the multiple source generator of the present invention has, in addition to the features discussed hereinbefore, the following advantages, many of which are interrelated:

(1) compatibility with the split, capacitive patient electrode 36;
(2) decreased power supply requirements, since no more than one of the generators is supplying energy to the patient at one time;
(3) because each source is optimized for only one function, it is possible to design each source for optimum reliability and performance;
(4) triple RF sources with high frequency desiccation and low frequency fulguration and cutting;
(5) compatibility with the return fault circuitry of FIG. 9;
(6) low frequency spark detection as a means of improving the return fault circuitry of FIG. 9 and as a means of detecting unsafe levels of neuromuscular stimulation;
(7) three mode hand switching made possible by feedback techniques which allow all three electrosurgical modes from a common output circuit;
(8) fulgurate only and cut only modes which do not desiccate and thereby avoid deep necrosis; and
(9) desiccate only mode for neurosurgery and the like.

What is claimed is:

1. An electrosurgical generator for use with a patient comprising
   first and second electrical power generating means;
   a common output circuit connected to said first and second electrical power generating means, said common output circuit including (a) an active lead and an active electrode connected thereto and (b) a patient lead and a patient electrode connected thereto;
   said first electrical power generating means (a) producing a voltage on said active electrode, the magnitude of which is sufficiently high to permit arcing from the active electrode to said patient and (b) including current limiting means for limiting the current through said patient to an arcing only value at which desiccation of the patient's tissue is not likely when said active electrode contacts the patient's tissue; and
   said second electrical power generating means (a) producing a current through said patient, the magnitude of which is sufficiently high to permit desiccation of the patient's tissue when said active electrode contacts the patient's tissue and (b) including voltage limiting means for limiting the voltage on said active electrode to a desiccate only value at which arcing from the active electrode to said patient is not likely.

2. A generator as in claim 1 where said first electrical power generating means includes selector means for selectively generating a first substantially continuous waveform signal suitable for cutting the patient's tissue or a second signal which comprises a train of bursts of radio frequency energy suitable for fulgurating said patient's tissue.

3. A generator as in claim 2 including a hand held electrosurgical instrument mounting said active electrode, said instrument including switching means to selectively actuate said selector means and said second electrical power generating means.

4. A generator as in claim 1 wherein said first electrical power generating means generates a first substantially continuous waveform signal suitable for cutting the patient's tissue and where said generator includes a third electrical power generating means for generating a second signal which comprises a train of bursts of radio frequency energy suitable for fulgurating said patient's tissue, said common output circuit also being connected to said third electrical power generating means.

5. A generator as in claim 4 including a hand held electrosurgical instrument mounting said active electrode, said instrument including switching means to selectively actuate said first, second and third electrical power generating means.

6. A generator as in claim 4 where said first electrical power generating means includes means for delivering 100 watts of power to a 3000 ohm load connected across said active and patient electrodes.

7. A generator as in claim 4 where said third electrical power generating means includes means for delivering 125 watts of power to a 5000 ohm load connected across said patient and active electrodes.

8. A generator as in claim 1 where second electrical power generating means includes means for providing one ampere of current into a 100 ohm load connected across said active and patient electrodes.

9. A generator as in claim 1 where said current limiting means limits the patient current to a value less than approximately 200 ma RMS.

10. A generator as in claim 1 including means for simultaneously actuating both said first and second electrical power generating means so that the second electrical power generating means can effect desiccation of the patient's tissue to thereby permit the initiation of said arcing from the active electrode.

11. A generator as in claim 1 where said first electrical power generating means includes first power adjusting means for adjusting the output power delivered to said output circuit and where said current limiting means includes feedback means for providing a feedback signal from said output circuit, said first power adjusting means being responsive to said feedback signal to thereby limit said patient current to said arcing only value.

12. A generator as in claim 11 where the response time of said feedback means is no greater than 10 ms.

13. A generator as in claim 11 where said second electrical power generating means includes second power adjusting means for adjusting the output power delivered to said output circuit and where said voltage limiting means includes feedback means for providing a feedback signal from said output circuit, said second power adjusting means being responsive to said feedback signal to thereby limit said active electrode voltage to said desiccate only value.

14. A generator as in claim 13 where the response time of said feedback means of the voltage limiting means is less than 10 ms.

15. A generator as in claim 1 where said second electrical power generating means includes power adjusting means for adjusting the output power delivered to said output circuit and where said voltage limiting means includes feedback means for providing a feedback signal from said output circuit, said second power adjusting means being responsive to said feedback signal to thereby limit said active electrode voltage to said desiccate only value.

16. A generator as in claim 15 where the response time of said feedback means is no greater than 10 ms.

17. A generator as in claim 1 where said patient electrode comprises at least one electroconductive substrate having a dielectric layer of electro-insulative material disposed thereon.

18. A generator as in claim 17 where said patient electrode comprises a first electroconductive substrate separated from a second electroconductive substrate, said dielectric layer being disposed on said first and second electroconductive substrates.

19. A generator as in claim 17 where the fundamental frequency of operation of said second electrical power generating means is sufficiently high to maintain the voltage on said patient below a predetermined level.

20. A generator as in claim 19 where said fundamental frequency is about 2.2 MHz.

21. A generator as in claim 19 where said fundamental frequency is greater than that of said first electrical power generating means.

22. A generator as in claim 21 where the fundamental frequencies of said first and second electrical power generating means are about 750 KHz and 2.2 MHz respectively.

23. A generator as in claim 19 where said patient lead and said patient electrode comprise a series LC circuit which resonates at the approximately said fundamental frequency.

24. A generator as in claim 17 including an inductor disposed in series with said patient lead so that said patient lead, said inductor and said patient electrode comprise a series LC circuit which resonates approximately at the fundamental frequency of operation of said first electrical power generating means.

25. A generator as in claim 1 including a hand held electrosurgical instrument mounting said active electrode, said instrument including switching means to selectively actuate said first and second electrical power generating means.

26. A generator as in claim 1 including first and second transformers, the primaries of which are respectively connected to said first and second electrical power generating means and the secondaries of which are connected in series in said common output circuit.

27. A generator as in claim 1 where said active electrode comprises a needle.

28. A generator as in claim 1 including arc detecting means for detecting low frequency components of the current in said common output circuit, said low frequency currents being capable of effecting neuromuscular stimulation of said patient and threshold means responsive to said arc detecting means for generating an output signal when said low frequency currents exceed a predetermined threshold.

29. A generator as in claim 1 including arc detecting means for detecting whether arcing is occurring in said common output circuit, patient lead current detecting means for detecting whether current is flowing in said patient lead and means responsive to said arc detecting means and said patient lead current detecting means for generating an output signal whenever an arcing is occurring in the common output circuit but current is not flowing in the patient lead.

30. An electrosurgical generator for use with a patient comprising
  first and second electrical power generating means;
  a common output circuit connected to said first and second electrical power generating means, said common output circuit including (a) an active lead and an active electrode connected thereto and (b) a patient lead and a patient electrode connected thereto;
  said first electrical power generating means (a) producing a voltage on said active electrode, the magnitude of which is sufficiently high to permit arcing from the active electrode to said patient; said
  said second electrical power generating means (a) producing a current through said patient, the magnitude of which is sufficiently high to permit desiccation of the patient's tissue when said active electrode contacts the patient's tissue and (b) including voltage limiting means for limiting the voltage on said active electrode to a desiccate only value at which arcing from the active electrode to said patient is not likely.

31. A generator as in claim 30 where said second electrical power generating means includes power adjusting means for adjusting the output power delivered to said output circuit and where said voltage limiting means includes feedback means for providing a feedback signal from said output circuit, said power adjusting means being responsive to said feedback signal to thereby limit said active electrode voltage to said desiccate only value.

32. A generator as in claim 31 where said feedback means includes means for providing a positive current feedback signal.

33. A generator as in claim 31 where the response time of said feedback means is no greater than 10 ms.

34. A generator as in claim 30 including a hand held electrosurgical instrument mounting said active electrode, said instrument including switching means to selectively actuate said first and second electrical power generating means.

35. A generator as in claim 30 including first and second transformers, the primaries of which are respectively connected to said first and second electrical power generating means and the secondaries of which are connected in series in said common output circuit and where the output impedance of said first transformer is sufficiently high to limit the current through said patient to an arcing only value at which desiccation of the patient's tissue is not likely when said active electrode contacts the patient's tissue.

36. An electrosurgical generator for use with a patient comprising first and second electrical power generating means;
a common output circuit connected to said first and second electrical power generating means, said common output circuit including (a) an active lead and an active electrode connected thereto and (b) a patient lead and a patient electrode connected thereto;
said first electrical power generating means (a) producing a voltage on said active electrode, the magnitude of which is sufficiently high to permit arcing from the active electrode to said patient and (b) including current limiting means for limiting the current through said patient to an arcing only value at which desiccation of the patient's tissue is not likely when said active electrode contacts the patient's tissue; and
said second electrical power generating means (a) producing a current through said patient, the magnitude of which is sufficiently high to permit desiccation of the patient's tissue when said active electrode contacts the patient's tissue.

37. A generator as in claim 36 where said first electrical power generating means includes first power adjusting means for adjusting the output power delivered to said output circuit and where said current limiting means includes feedback means for providing a feedback signal from said output circuit, said first power adjusting means being responsive to said feedback signal to thereby limit said patient current to said arcing only value.

38. A generator as in claim 37 where the response time of said feedback means is no greater than 10 ms.

39. A generator as in claim 36 where said active electrode comprises a needle.

40. A generator as in claim 39 where said current limiting means includes arc detecting means for detecting whether arcing is occurring in said common output circuit, said first power adjusting means being responsive to said arc detecting means to allow said patient current to rise to said arcing only value only if said arc detecting means detects said arcing in the common output circuit.

41. A generator as in claim 36 including arc detecting means for detecting low frequency components of the current in said common output circuit, said low frequency currents being capable of effecting neuromuscular stimulation of said patient and threshold means responsive to said arc detecting means for generating an output signal when said low frequency currents exceed a predetermined threshold.

42. A generator as in claim 36 including arc detecting means for detecting whether arcing is occurring in said common output circuit, patient lead current detecting means for detecting whether current is flowing in said patient lead and means responsive to said arc detecting means and said patient lead current detecting means for generating an output signal whenever an arcing is occuring is the common output circuit but current is not flowing in the patient lead.

43. A generator as in claim 36 where said current limiting means limits the patient current to a value less than approximately 200 ma. RMS.

44. A generator as in claim 36 including first and second transformers, the primaries of which are respectively connected to said first and second electrical power generating means and the secondaries of which are connected in series in said common output circuit and where the output impedance of said second transformer is sufficiently low to limit the voltage on said active electrode to a desiccate only value at which arcing from the active electrode to said patient is not likely.

45. A generator as in claim 44 where the impedance of the secondary winding of said first transformer in series with the secondary winding of said second transformer is also sufficiently low to limit said active electrode voltage to said desiccate only value.

46. An electrosurgical generator for use with a patient comprising an electrical power generating means;
an output circuit connected to said electrical power generating means, said output circuit including (a) an active lead and an active electrode connected thereto and (b) a patient lead and a patient electrode connected thereto; and
said electrical power generating means (a) producing a voltage on said active electrode, the magnitude of which is sufficiently high to permit arcing from the active electrode to said patient and (b) including current limiting means for limiting the current through said patient to an arcing only value at which desiccation of the patient's tissue is not likely when said active electrode contacts the patient's tissue.

47. A generator as in claim 46 where said electrical power generating means includes power adjusting means for adjusting the output power delivered to said output circuit and where said current limiting means includes feedback means for providing a feedback signal from said output circuit, said power adjusting means being responsive to said feedback signal to thereby limit said patient current to said arcing only value.

48. A generator as in claim 47 where the response time of said feedback means is no greater than 10 ms.

49. A generator as in claim 46 where said active electrode comprises a needle.

50. A generator as in claim 49 where said current limiting means includes arc detecting means for detecting whether arcing is occurring in said output circuit, said power adjusting means being responsive to said arc detecting means to allow said patient current to rise to said arcing only value if said arc detecting means detects said arcing in the output circuit.

51. A generator as in claim 46 including arc detecting means for detecting low frequency components of the current in said output circuit, said low frequency currents being capable of effecting neuromuscular stimulation of said patient and threshold means responsive to said arc detecting means for generating an output signal when said low frequency currents exceed a predetermined threshold.

52. A generator as in claim 46 including arc detecting means for detecting whether arcing is occurring in said output circuit, patient lead current detecting means for detecting whether current is flowing in said patient lead and means responsive to said arc detecting means and said patient lead current detecting means for generating an output signal whenever an arcing is occurring in the output circuit but current is not flowing in the patient lead.

53. A generator as in claim 46 where said current limiting means limits the patient current to a value less than approximately 200 ma. RMS.

54. An electrosurgical generator for use with a patient comprising an electrical power generating means;

an output circuit connected to said electrical power generating means, said output circuit including (a) an active lead and an active electrode connected thereto and (b) a patient lead and a patient electrode connected thereto; and said electrical power generating means (a) producing a current through said patient, the magnitude of which is sufficiently high to permit desiccation of the patient's tissue when said active electrode contacts the patient's tissue, (b) including voltage limiting means for limiting the voltage on said active electrode to a desiccate only value at which arcing from the active electrode to said patient is not likely, and (c) including adjusting means for adjusting the output power delivered to said output circuit and where said voltage limiting means includes feedback means for providing a positive current feedback signal from said output circuit, said power adjusting means being responsive to said positive current feedback signal to thereby limit said active electrode voltage to said desiccate only value.

55. An electrosurgical generator for use with a patient comprising an electrical power generating means;

an output circuit connected to said electrical power generating means, said output circuit including (a) an active lead and an active electrode connected thereto and (b) a patient lead and a patient electrode connected thereto;

the output impedance of said electrical power generating means normally being sufficiently high to effect arcing from said active electrode to said patient;

switching means;

circuit means responsive to said switching means for lowering the said output impedance of said electrical power generating means and thereby limit the voltage on said active electrode to a desiccate only value at which arcing from the active electrode to said patient is not likely.

56. A generator as in claim 55 where said circuit means comprises a feedback circuit connected from said output circuit to said electrical power generating means.

57. A generator as in claim 55 including an electrosurgical instrument where said active electrode and said switching means are disposed on said electrosurgical instrument.

58. An electrosurgical generator for use with a patient comprising an electrical power generating means;

an output circuit connected to said electrical power generating means, said output circuit including (a) an active lead and an active electrode connected thereto and (b) a patient lead and a patient electrode connected thereto;

said electrical power generating means producing a voltage on said active electrode, the magnitude of which is sufficiently high to permit arcing from the active electrode to said patient;

arc detecting means for detecting low frequency components of the current in said output circuit, said low frequency currents being capable of effecting neuromuscular stimulation of said patient; and threshold means responsive to said arc detecting means for generating an output signal when said low frequency currents exceed a predetermined threshold.

59. An electrosurgical generator for use with a patient comprising an electrical power generating means;

an output circuit connected to said electrical power generating means, said output circuit including (a) an active lead and an active electrode connected thereto and (b) a patient lead and a patient electrode connected thereto;

said electrical power generating means producing a voltage on said active electrode, the magnitude of which is sufficiently high to permit arcing from the active electrode to said patient;

arc detecting means for detecting whether arcing is occurring in said output circuit;

patient lead current detecting means for detecting whether current is flowing in said patient lead; and means responsive to said arc detecting means and said patient lead current detecting means for generating an output signal whenever an arcing is occurring in the output circuit but current is not flowing in the patient lead.

* * * * *